[19] United States Patent
Manankov

[11] 4,291,497
[45] Sep. 29, 1981

[54] METHOD OF INTRODUCING CHEMICAL AGENTS INTO PLANTS

[76] Inventor: Mikhail K. Manankov, Simferopolsky raion, selo Molodezhnoe, ulitsa Polevaya 6,, Krymskaya oblast, U.S.S.R.

[21] Appl. No.: 91,582

[22] Filed: Nov. 5, 1979

[30] Foreign Application Priority Data

Feb. 26, 1979 [SU] U.S.S.R. .............................. 2723951

[51] Int. Cl.$^3$ ........................... A01G 1/00; C05C 9/00
[52] U.S. Cl. ........................................... 47/58; 47/7; 47/57.5; 47/DIG. 13; 71/88; 71/122
[58] Field of Search .................. 71/DIG. 1, 122, 88; 47/7, 58, 57.5, DIG. 13, DIG. 4-5

[56] References Cited

U.S. PATENT DOCUMENTS

| | | | |
|---|---|---|---|
| 1,860,255 | 5/1932 | L'Hommedieu | 47/7 |
| 1,990,966 | 2/1935 | Volck | 47/DIG. 13 |
| 2,913,372 | 11/1959 | Velde et al. | 71/DIG. 1 |
| 3,420,617 | 1/1969 | Kimm | 47/57.5 X |
| 4,033,747 | 7/1977 | Young | 47/DIG. 13 |

OTHER PUBLICATIONS

Chem. Abstracts, vol. 42, 5603-5604, Burgdorf.

Primary Examiner—Robert E. Bagwill
Attorney, Agent, or Firm—Robert E. Burns; Emmanuel J. Lobato; Bruce L. Adams

[57] ABSTRACT

A method of introducing chemical agents into plants comprising application, onto plants, of preparations in the form of powders or solutions based on chemical agents and polyhydric alcohols or low-molecular carbohydrates. The method of the present inventions ensures a rapid penetration of a chemical agent into a plant or individual organs thereof in predetermined amounts thus enhancing efficiency of a chemical agent and ensuring an optimal use thereof.

23 Claims, No Drawings

METHOD OF INTRODUCING CHEMICAL AGENTS INTO PLANTS

FIELD OF THE INVENTION

The present invention relates to plant growing and, more specifically, to methods of introducing chemical agents into plants, i.e. compounds intended to effect on plants with the view to control their vital activity or prevent from diseases and pests, such as macro- and trace-elements, vitamins, phytohormones, plant growth inhibitors, preparations for the control of pests and diseases.

BACKGROUND OF THE INVENTION

In the art of plant breeding methods are known for introducing chemical agents into plants by way of application, onto plants, of preparations based on said chemical agents as powders or solutions. Application of preparations onto plants is effected by spraying, dusting, dipping individual organs of plants into the preparation solution (cf. R. J. Weaver, Plant Growth Substances in Agriculture., University of California, Davis, W. H. Freeman and Company; 1972; F. L. Kalinin, Yu. G. Mereyhinski, "Plant Growth Regulators" (in Russian), Naukova Dumka Publishing House, Kiev, 1965; V. F. Verzilov, "Plant Growth Regulators and Their Use in Plant Growing", "Nauka" Publishing House, Moscow, 1971).

Said prior art method do not provide for a fast penetration of a chemical agent in predetermined amounts into a plant, thus lowering the efficiency of action of the chemical agent and results in an economically ineffective use thereof. Furthermore, the modes of application of preparations as employed in the prior art methods do not make it possible in certain cases to ensure a prescribed application of the preparation on individual organs of a plant which should be treated with said chemical agents. This, in turn, also results in an ineffective consumption of the chemicals.

SUMMARY OF THE INVENTION

It is an object of the present invention to provide a method of introducing chemical agents into plants which ensures the rapid penetration of the chemical agent into a plant or individual organs thereof in predetermined amounts and, thereby, increases the efficiency of action of the chemical agent and provides for an economically effective use thereof.

This and other objects of the present invention are accomplished by the provision of a process for introducing chemical agents into plants by way of application, on the plants, of preparations based on chemical agents in the form of powers or solutions, wherein in accordance with the present invention use is made of preparations incorporating also polyhydric alcohols or low-molecular carbohydrates.

The polyhydric alcohols employed in compositions of the preparations according to the present invention and low-molecular products are similar to metabolism products in plants, wherefore said alcohols and low-molecular carbohydrates readily penetrate into plants and are transported therein along with chemical agents. Said chemical agents can be introduced in predetermined amounts both into the plant as a whole and into individual organs thereof.

The present invention makes it possible to increase the efficiency of the action of chemical agents and ensure an effective use thereof.

Among polyhydric alcohols it is advisable to use dulcitol, arabitol, mannitol, sorbitol.

As low-molecular carbohydrates it is advisable to use saccharose, glucose, fructose.

Powder-like preparations are advisable to be applied onto plants locally by means of an adhesive tape with a powder-like preparation predeposited thereon. After such application of an adhesive tape there occurs dissolution of the powder on the plant surface in transpiration moisture of the plant. The solution thus formed is readily transported into the plants.

This application of powder-like preparations to plants by means of an adhesive tape can be effected under any weather conditions, but this technique is espeically effective under conditions of a low and high atmospheric humidity. For instance, upon heavy rainfall, the adhesive tape prevents the preparation from being washed-off and, thereby, contributes to its effective utilization.

Application of powder-like preparations onto plants by means of an adhesive tape is also advantageous under the conditions of intensive solar radiation. Under such conditions it is inexpedient to apply preparations on plants in the form of solutions, since drops of the preparation solution concentrate solar rays thus causing burns on plants.

The use of an adhesive tape makes it possible to apply the preparation locally on the individual organs and regions of plants in predetermined amounts.

To introduce a chemical agent into the given plant organ with a definite purpose (e.g. to stimulate fructification and shoots growth), it is preferable that preparations be applied to the basal portion of plant organs.

It is advisable to use preparations containing, as chemical agents, macroelements, trace elements, vitamins, phytohormones, plant growth inhibitors, agents for controlling pests and plant diseases or various combinations thereof.

It is advisable to use preparations containing, as macroelements, nitrogen, phosphorus potassium.

As trace elements it is advisable to incorporated into compositions of the preparations according to the present invention such elements as boron, zinc or manganese.

As vitamins the preparation should contain thiamine or ascorbic acid.

As phytohormones said preparations should contain gibberellin, auxin or cytoquinine.

As plant growth inhibitors the preparations should preferably contain chlorocholine chloride, 2,4-dichlorophenoxy-acetic acid or 2-methyl-4-chlorophenoxyacetic acid.

It is desirable to use preparations containing, as agents for treating plant diseases, copper sulphate, formaldehyde, para-rodaniline, ethylmercurophosphate, penicillin or streptomycin.

As agents for plant pest control, it is advisable that the preparations according to the present invention contain thiophos, methylmercaptophos or octamethyl.

In order to provide a more effective consumption of polyhydric alcohols and low-molecular carbohydrates, it is advisable to introduce, into compositions of the preparations according to the present invention, a filler preferably such as china clay, talc or plant ash.

DETAILED DESCRIPTION OF THE INVENTION

The method of introducing chemical agents into plants is effected in the following manner.

Preparations based on chemical agents, as well as polyhydric alcohols and low-molecular carbohydrates, are applied to plants in the form of powders or solutions.

Preparations in the form of solutions are made by dissolving a chemical agent and a polyhydric alcohol or a low-molecular carbohydrates in suitable solvents. As the solvents use is generally made of water, ethanol, ethylacetate and other solvents or various mixtures thereof. Thus, a preparation in the form of a solution based on a chemical agent, i.e. gibberellin and a low-molecular carbohydrate, i.e. saccharose, is prepared by dissolving separately gibberellin in ethanol and saccharose—in water, whereafter the solutions are combined.

Preparations in the powder-like form are prepared, e.g. by way of a mechanical blending of a powder-like chemical agent and a powder of a polyhydric alcohol or a low-molecular carbohydrate.

Preparations in the form of powders should be preferably made by way of dissolution of a chemical agent in a solvent, followed by introducing a powder of a polyhydric alcohol or a low-molecular carbohydrate into the solution under thorough mixing. As a result, a concentrated solution or a slurry-like mass is obtained, whereafter the solvent is removed therefrom. The resulting dry homogeneous mass is disintegrated to powder. Thus, in the preparation of a powder-like formulation consisting of a chemical agent, i.e. gibberellin, and a low-molecular carbohydrate, i.e. saccharose, gibberellin is first dissolved in ethanol, whereafter saccharose is added to the solution under thorough stirring. As a result, a slurry-like mass is obtained, wherefrom the solvent is distilled-off. The resulting dry homogeneous mass is finely divided to a powder-like condition.

Preparation in the form of solutions are applied onto plants by way of, for example, spraying or dipping individual organs of plants into a solution of the preparation.

Powder-like preparations are applied onto plants by dusting or by means of an adhesive tape (such as medical adhesive plaster) which is adhered to plants. A powder-like preparation is preliminary deposited onto the adhesive surface of the plaster by atomization.

The method according to the present invention makes it possible to effectively introduce chemical agents into different plants such as fruit-berry plants (apple trees, pear trees, grapes, currant, straw-berry); grain crops (such as wheat, barley, proso); vegetable crops (tomatoes, cabbage); decorative plants (such as roses, pinks, lilac); forest plants (oak, pine trees).

Chemical agents are introduced into plants with different purposes, e.g. for stimulation of fructification, stimulation or inhibition of growth of plants or individual organs thereof, increasing the amount of pigments in leaves; stimulation of generative growth of plants; control of diseases and plant pests. Depending on the selected purpose, chemical agents are employed during various periods of plant vegetation; subjected to the treatment with the preparation is either the plant as a whole, or individual organs and regions thereof.

For a better understanding of the present invention some specific Examples are given hereinbelow by way of illustration.

EXAMPLE 1

A composition based on a macroelement is prepared in the form of a solution, i.e. nitrogen, and a low-molecular carbohydrate such as saccharose. To this end, 4 parts by weight of ammonium nitrate and 5 parts by weight of saccharose are dissolved in 91 parts by weight. The thus-prepared composition is applied, by spraying, on wheat plants in the spring time when the plants are in the stage of leaf-tube formation for the purpose of stimulation of wheat growth and fructification thereof.

As a result, the yield of the test wheat has been increased by 15.6% as compared to that of the wheat non-treated by the preparation.

For the purpose of comparison, a preparation on the basis of the same macroelement, i.e. nitrogen, is formulated, though without saccharose. To this end, 4 parts of ammonium nitrate are dissolved in 96 parts by weight of water.

The thus-made preparation is used as described above.

As a results, the cropping power of the treated wheat is increased by 5.7% as compared to that of the wheat non-treated with the preparation.

EXAMPLE 2

A composition based on phosphorus (macroelement) and a low-molecular carbohydrate, i.e. fructose is prepared in the form of a solution. To this end, 8 partsby weight of superphosphate (calculated for $P_2O_5$) and 8 parts by weight of fructose are dissolved in 84 parts of water.

The thus-prepared composition is employed as described in the foregoing Example 1. As a result, the cropping power of the treated wheat is increased by 12.7% as compared to that of the wheat non-treated with the preparation.

For the purpose of comparison, the preparation based on the same macroelement (phosphorus) is formulated, though without using fructose. To make the preparation, 8 parts by weight of superphosphate are dissolved in 92 parts by weight of water.

The thus-made preparation is employed as described in Example 1 hereinbefore. As a result, the cropping power of the treated wheat is increased by 4.8% as compared to that of the wheat non-treated with the preparation.

EXAMPLE 3

A composition based on a macroelement (potassium) and a low-molecular carbohydrate (glucose) is prepared in the form of a solution. To make the preparation, 4 parts by weight of potassium chloride and 5 parts by weight of glucose are dissolved in 91 parts by weight of water.

The thus-made preparation is used as described in Example 1 hereinbefore. As a result, the cropping power of the treated wheat is increased by 10.3% as compared to that of the wheat not subjected to the treatment with the preparation.

For the purpose of comparison, a preparation is made on the basis of the same macroelement, i.e. potassium, though without using glucose. To this end, 4 parts by weight of potassium chloride are dissolved in 96 parts by weight of water.

The thus-produced preparation is employed in a manner similar to that described in Example 1. As a result, the cropping power of wheat is increased by 4.2% as compared to that of the wheat non-treated with the preparation.

EXAMPLE 4

A preparation is formulated on the basis of macroelements such as nitrogen, phosphorus and potassium, as well as a low-molecular carbohydrate (saccharose). For this purpose, 4 parts of urea, 4 parts of superphosphate, 2 parts by weight of potassium chloride and 8 parts by weight of saccharose are dissolved in 82 parts by weight of water.

The thus-made composition is applied by spraying on grape bushes 15-20 days after completion of blossoming in order to improve fructification and increase the sugar-content of grapes.

As a result, cropping power of grapes is increased by 17% and sugar-content of grape berries—by 1.3% as compared to corresponding characteristics of grape bushes non-treated with the preparation.

For the purpose of comparison, a preparation in the form of a solution is made which contains the same macroelements, i.e. nitrogen, potassium and phosphorus, but has no saccharose. To this end, 4 parts by weight of urea, 4 parts by weight of superphosphate and 2 parts by weight of potassium chloride are dissolved in 90 parts by weight of water.

The thus-produced preparation is applied onto grape bushes in a manner similar to that described hereinabove. As a result, the sugar content of grapes is increased by 0.7% and croppin power—by 7.6% as compared to corresponding characteristics of grapes on bushes non-treated with the preparation.

EXAMPLE 5

A preparation based on macroelements, i.e. nitrogen, phosphorus, potassium and a low-molecular carbohydrate, i.e. glucose, is produced. To do so, 2 parts of ammonium nitrate, 4 parts by weight of superphosphate, 2 parts by weight of potassium chloride and 5 parts by weight of glucose are dissolved in 87 parts by weight of water.

The thus-prepared formulation is sprayed on tomato plants during the blossoming period and fruit-setting in order to stimulate fruit-formation.

As a result, the yield of tomatoes is increased by 18.6% as compared to that of tomatoes non-treated with the preparation.

For the purpose of comparison a preparation in the form of a solution is made on the basis of the same macroelements, i.e. nitrogen, phosphorus, potassium, though without using glucose. To this end, 2 parts by weight of ammonium nitrate, 4 parts by weight of superphosphate and 2 parts by weight of potassium chloride are dissolved in 92 parts by weight of water.

The thus-produced preparation is applied to tomato plants in a manner similar to that described hereinabove. As a result, the yield of tomato plants is increased by 7.8% as compared to that of tomatoes non-treated with the preparation.

EXAMPLE 6

A preparation based on macroelements such as nitrogen, phosphorus, potassium and a polyhydric alcohol, i.e. mannitol is made in the form of a solution. To this end, 2 parts by weight of ammonium nitrate, 4 parts by weight of superphosphate, 2 parts by weight of potassium chloride and 4 parts by weight of mannitol are dissolved in 88 parts by weight of water.

The thus-prepared composition is applied onto tomato plants in a manner similar to that described in Example 5 hereinabove. As a result, the yield of tomato plants is increased by 16.3% as compared to that of tomato plants non-treated with the preparation.

For the purpose of comparison there is produced a preparation by way of dissolution in 92 parts by weight of water of the same macroelements and in the same amounts as above, but without mannitol.

The resulting preparation is applied onto tomato plants, following the procedure of Example 5 hereinbefore. As a result, the cropping power of tomato plants is increased by 7.8% as compared to that of tomato plants non-treated with the preparation.

EXAMPLE 7

A powder-like preparation is formulated on the basis of macroelements, i.e. nitrogen and phosphorus, a low-molecular carbohydrate, i.e. saccharose, and a filler which is talc. To this end, 2 parts by weight of urea and 3 parts by weight of superphosphate are dissolved in 100 parts by weight of water. To the resulting solution is added 12 parts by weight of saccharose under thorough stirring. In this manner, a slurry-like mass is obtained to which is then added under agitation 83 parts by weight of talc. The final mass is dried and ground to a powder-like condition.

The thus-produced preparation is used to treat by dusting, after sprinkling, tomato plants during the period of blossoming and fruit-setting in order to stimulate fruit-formation.

As a result, the cropping power of tomatoes is increased by 14.7% as compared to that of tomato plants non-treated with the preparation.

For this purpose of comparison, a powder-like preparation is made on the basis of the same macroelements, with the only difference, that saccharose is excluded from the composition and talc is used in the amount of 95 parts by weight.

The thus-produced preparation is applied onto tomato plants in a manner similar to that described hereinabove. As a result, the cropping power of tomatoes is increased by 6.3% as compared to that of tomato plants non-treated with the preparation.

EXAMPLE 8

A powder-like preparation is produced on the basis of macroelements, i.e. nitrogen, phosphorus and potassium, and a low-molecular carbohydrate (saccharose). To this end, 2 parts by weight of sodium nitrate, 6 parts by weight of superphosphate, 2 parts by weight of potassium chloride are dissolved in 100 parts by weight of water. To the resulting solution is added 90 parts by weight of saccharose under thorough stirring. The thus-produced slurry-like mass is dried and finely divided to a powder-like conditions.

The resulting preparation is applied to an adhesive tape, i.e. medical adhesive plaster, at the rate of 5 mg of the preparation per 1 cm$^2$ of the tape. Then the adhesive tape with the preparation deposited thereon is cut to strips with the dimensions of 2×3 cm. Said strips are fixed in a ringlike manner to basal parts of shoots of grape 10 days after completion of blossoming.

As a result, the cropping yield of grapes is increased by 11.3% as compared to that of grapes non-treated with the preparation.

For the purpose of comparison, a powder-like preparation is produced on the basis of the same macroelements, with the only exception that saccharose is excluded from the composition and talc is added in the amount of 90 parts by weight (the filler - talc is added with the view to preserve the same concentration of macroelements as in the saccharose-containing preparation).

Deposition of the thus-produced preparation onto an adhesive tape, cutting the latter to strips and fixation of said strips to basal parts of grape shoots are effected as described hereinabove. As a result, the cropping power of grapes is increased by 6.3% as compared to that for grapes non-treated with the preparation.

EXAMPLE 9

A powder-like preparation is produced which is based on a trace element, i.e. boron, a low-molecular carbohydrate, i.e. glucose, and a filler - china clay. To this end, 0.025 part by weight of boric acid is dissolved in 100 parts by weight of water. Into the resulting solution there are added, under thorough stirring, 10 parts by weight of glucose and, thereafter, 89.975 parts by weight of china clay. The thus-obtained slurry-like mass is dried and finely divided to a powder-like condition.

With the resulting preparation grape bushes are dusted during the blossoming period in order to increase the amount of grapes in a bunch and total cropping yield.

As a result, the amount of grapes in a bunch is increased by 26% and cropping yield—by 18.7% as compared to corresponding characteristics of grape bushes non-treated with the preparation.

For the purpose of comparison a powder-like preparation is produced on the basis of the same trace element, with the only exception that glucose is not incorporated into the composition of the preparation and china clay is used in the amount of 99.975 parts by weight.

The thus-produced preparation is applied to grape bushes in a manner similar to that described hereinabove. As a result, the amount of grapes in a bunch is increased by 6.1% and cropping power—by 4.8% as compared to corresponding characteristics of grape bushes non-treated with the preparation.

EXAMPLE 10

In a manner similar to that described in the foregoing Example 9 a powder-like preparation is produced on the basis of a microelement (boron), a low-molecular carbohydrate (saccharose) and a filler (talc). To this end, 0.025 parts by weight of boric acid is dissolved in 100 parts by weight of water. Into the resulting solution under thorough stirring there are added 10 parts by weight of saccharose and then 89.975 parts by weight of talc. The resulting slurry-like mass is dried and finely divided to a powder-like condition.

The thus-produced preparation is used for dusting of tomato plants during the period of blossoming and fruit setting in order to increase the number of fruit in a raceme and obtain a higher cropping power of tomatoes.

As a result, the number of fruit in a raceme is increased by 16.5% and cropping power—by 12.3% as compared to corresponding characteristics of tomato plants non-treated with the preparation.

For the purpose of comparison, a powder-like preparation is produced on the basis of the same trace element with the only exception that saccharose is not present in the composition of the preparation and talc is used in the amount of 99.975 parts by weight.

The thus-prepared composition is applied onto tomato plants following the procedure described hereinabove. As a result, the number of fruit in a raceme is increased by 7.3% and cropping power—by 5.9% as compared to corresponding characteristics of tomato plants non-treated with the preparation.

EXAMPLE 11

A powder-like preparation is produced on the basis of trace elements, i.e. manganese and zinc, a polyhydric alcohol (sorbitol) and a filler (talc). To this end, 0.1 part by weight of manganese sulphate and 0.1 part by weight of zinc sulphate are dissolved in 100 parts by weight of water. Into the resulting solution under thorough stirring there are added 10 parts by weight of sorbitol and then 89.8 parts by weight of talc. The resulting slurry-like mass is dried and ground to a powder-like condition.

The thus-produced preparation is used for treatment by dusting of apple trees during the period of blossoming in order to stimulate the process of fruit-formation. As a result, the number of set fruits is increased by 18% and yield —by 16.2% as compared to the number of set fruits and yield of apples from the trees non-treated with the preparation.

For the purpose of comparison, a powder-like preparation on the basis of the same trace elements is produced, except that sorbitol is not used in the composition of the preparation and talc is used in the amount of 99.8 parts by weight.

The thus-produced preparation is applied onto apple trees as described hereinabove. As a result, the number of set fruits is increased by 5.3% and yield—by 4.1% as compared to the number of set fruits and cropping power of apple trees non-treated by the preparation.

EXAMPLE 12

A preparation in the form of a solution is prepared on the basis of trace elements (manganese and boron) and a low-molecular carbohydrate (glucose). To this end, 0.1 part by weight of manganese sulphate and 0.05 part by weight of boric acid are dissolved in 89.85 parts by weight of water. Into the resulting solution under thorough stirring there are added 10 parts by weight of glucose.

This preparation in the form of a solution is used for spraying cucumber plants during blossoming in order to increase cropping power thereof.

As a result the cropping power is increased by 12% as compared to that of cucumber plants non-treated with the preparation.

For the purpose of comparison, a powder-like preparation is produced on the basis of the same trace elements with the only difference that glucose is not used in the composition of the preparation and water is taken in the amount of 99.85 parts by weight.

The thus-produced preparation is applied onto cucumber plants in a manner similar to that described hereinabove. As a result, the cropping power is increased by 6.3% as compared to that of cucumber plants non-treated with the preparation.

EXAMPLE 13

A powder-like preparation is produced on the basis of a trace element (boron), an agent for controlling grape mildew (copper sulphate) and a low-molecular carbohydrate (saccharose). To this end, 0.05 part by weight of boric acid and 0.75 part by weight of copper sulphate are dissolved in 100 parts by weight of water. Into the resulting solution 99.2 parts by weight of saccharose are introduced under thorough stirring. The thus-prepared slurry-like mass is dried and finely divided to a powder-like condition.

The resulting powder-like preparation is deposited by dusting onto an adhesive tape at the rate of 5 mg of the preparation per 1 cm² of the tape surface area. Then the adhesive tape with the preparation deposited thereon is cut into strips with the dimensions 2×3 cm. Said strips are fixed to basal parts of grape inflorescences 10 days prior to the beginning of blossoming.

As a result, the amount of grapes in a bunch is increased by 21% and cropping power—by 20.6%, while injury of grapes with mildew is reduced by 70% as compared to similar characteristics of grape bushes non-treated with the preparation.

For the purpose of comparison a powder-like preparation is produced as described hereinabove on the basis of a trace element (boron), an agent for controlling grape mildew (copper sulphate), with the only exception that saccharose is not used in the composition of the preparation and the filter (talc) is added in the amount of 99.2 parts by weight.

Dusting of the preparation onto the adhesive tape, cutting thereof to pieces and fixation thereof to basal parts of inflorescences of grapes are effected following the above-described procedure. As a result, the amount of grapes in a bunch is increased by 8.8%, cropping power—by 5.7%, while injury of the plants with mildew is reduced by 12.3% as compared to corresponding characteristics of grape bushes non-treated with the preparation.

EXAMPLE 14

A preparation in the form of a solution is prepared on the basis of a vitamin (thiamine), a phytohormone (gibberellin) and a polyhydric alcohol (dulcitol). To this end, 0.00015 part by weight of thiamine, and 7 parts by weight of dulcitol are dissolved in 89.99 parts by weight of water, while 0.01 part by weight of gibberrellin is dissolved in 3 parts by weight of ethanol. The resulting solutions are combined.

By the preparation in the form of a solution there are sprayed inflorescences of a seedless variety of grapes during the period of mass blossoming.

As a result, the amount of grapes in a bunch is increased by 25% and yield—by 47% as compared to grape bushes non-treated with the preparation.

For the purpose of comparison a preparation in the form of a solution is prepared on the basis of the same vitamin and phytohormone, except that dulcitol is not used in the composition of the preparation and water is used in the amount of 96.99 parts by weight.

The thus-produced solution is applied onto inflorescences of grapes in a manner similar to that described hereinabove. As a result, the number of grapes in a bunch is increased by 11.5% and cropping power—by 26.1% as compared to bushes of grapes with the inflorescences non-treated by the preparation.

EXAMPLE 15

A preparation in the form of a solution is prepared on the basis of a phytohormone (gibberellin) and a polyhydric alcohol (arabitol). To this end, 0.010 part by weight of gibberellin is dissolved in 3 parts by weight of ethanol and 10 parts by weight of arabitol are dissolved in 86.090 parts by weight of water. The thus-prepared solutions are combined.

The preparation in the form of a solution prepared in this manner is used to spray inflorescences of seedless grape varieties during the period of mass blossoming.

As a result, the amount of grapes in a bunch is increased by 17.3% and cropping power—by 36.5% as compared to grape bushes with the inflorescences non-treated by the above preparation.

For the purpose of comparison a preparation is produced in the form of a solution on the basis of the same phytohormone, with the only exception that arabitol is not used in the composition of the preparation and water is employed in the amount of 96.090 parts by weight.

The thus-prepared solution is applied onto grape inflorescences in a manner similar to that described hereinabove. As a result, the amount of grapes in a bunch is increased by 10.2%, while cropping power—by 24.3% as compared to corresponding characteristics of grape bushes with inflorescences non-treated with the preparation.

EXAMPLE 16

A preparation in the form of a solution is produced on the basis of a vitamin (ascorbic acid), a phytohormone (gibberellin) and a polyhydric alcohol (dulcitol). To this end, 0.00015 part by weight of ascorbic acid and 10 parts by weight of dulcitol are dissolved in 86.9 parts by weight of water and 0.01 part by weight of gibberellin is dissolved in 3 parts by weight of ethanol. The resulting solutions are combined.

The preparation in the form of the thus-prepared solution is used to spray inflorescences of a seedless grape variety during the period of mass blossoming.

As a result, the amount of grapes in a bunch is increased by 28.3%, and cropping power—by 49.6% as compared to bushes of grapes with inflorescences non-treated with the preparation.

For the purpose of comparison a preparation in the form of a solution is produced on the basis of the same vitamin and phytohormone, with the only exception that dulcitol is not used in the composition of the preparation and water is used in the amount of 96.9 parts by weight.

The thus-prepared solution is applied onto grape inflorescences in a manner similar to that described hereinabove. As a result, the amount of grapes in a bunch is increased by 16.3% and cropping power—by 29.6% as compared to grape bushes with the inflorescences non-treated with the preparation.

EXAMPLE 17

A solution of a preparation is prepared on the basis of vitamins (thiamine and ascorbic acid) and a low-molecular carbohydrate (saccharose). To this end, 0.00015 part by weight of thiamine, 0.00015 part by weight of ascorbic acid and 10 parts by weight of saccharose are dissolved in 89.99 parts by weight of water.

The preparation in the form of the thus-prepared solution is used to spray inflorescences of grapes during the period of mass blossoming.

As a result, the number of grapes in a bunch is increased by 18.3% and cropping power—by 15.6% as compared to corresponding characteristics of grape bushes with inflorescences non-treated with the preparation.

For the purpose of comparison, a preparation in the form of a solution is produced on the basis of the same vitamins, with the only difference that saccharose is not used in the composition of the preparation and water is used in the amount of 99.99 parts by weight.

The resulting solution is sprayed onto grape inflorescences in a similar manner as that described above. As a result, the number of grapes in a bunch is increased by 6.9% and cropping power—by 7.3% as compared to corresponding characteristics of grape bushes with inflorescences non-treated with the preparation.

EXAMPLE 18

A powder-like preparation is produced on the basis of a phytohormone (gibberellin) and a polyhydric alcohol (dulcitol). To this end, 1 part by weight of gibberellin is dissolved in 5 parts by weight of ethanol. To the resulting solution is added 100 parts by weight of water and, thereafter, 99 parts by weight of dulcitol under thorough stirring. The thus-prepared slurry-like mass is dried and finely divided to a powder-like condition.

The preparation is applied onto an adhesive tape by dusting at the rate of 5 mg of the preparation per 1 cm$^2$ of the tape area. Then the adhesive tape with the preparation deposited thereon is cut to strips with the dimensions of 2×3 cm. These strips are fixed in a ring-like manner onto basal parts of grape shoots 15 days before the beginning of mass blossoming.

As a result, a good loosening of inflorescences and bunches is obtained thus resulting in reduced injury of grapes with gray mould by 65.3% and in an increased cropping power of grapes by 23.5% as compared to corresponding characteristics of grape bushes non-treated with the preparation.

For the purpose of comparison, a powder-like preparation is produced on the basis of the same phytohormone, with the only exception that dulcitol is not used in the composition of the preparation and the filler (talc) is added in the amount of 99 parts by weight.

Dusting of the preparation onto the adhesive tape, its cutting to strips and fixation thereof onto basal parts of grape shoots are effected in a manner similar to that described hereinabove. As a result, a less pronounced loosening of inflorescences and then of bunches is observed. Injury of grapes with gray mould is reduced by 19.6% and cropping power is increased by 7.9% as compared to similar characteristics of grape bushes non-treated with the preparation.

EXAMPLE 19

A powder-like preparation is produced on the basis of a phytohormone (gibberellin) and a polyhydric alcohol (mannitol). To this end, 1 part by weight of gibberellin is dissolved in 5 parts by weight of ethanol. To the resulting solution is added 100 parts by weight of water and then 99 parts by weight of mannitol. The resulting slurry-like mass is dried and disintegrated to a powder-like condition.

The thus-produced preparation is deposited by dusting onto an adhesive tape at the rate of 5 mg per 1 cm$^2$ of the tape. Then the adhesive tape with the preparation deposited thereon is cut to strips with the dimensions of 2×3 cm. Said strips are fixed in a ring-like manner to basal parts of tomato racemes 5 days after the beginning of mass blossoming.

As a result, the number of fruits in tomato racemes is increased by 18% and cropping power—by 15.6% as compared to tomato plants non-treated with the preparation.

For the purpose of comparison, a powder-like preparation is produced on the basis of the same phytohormone, with the only difference that dulcitol is not used in the composition of the preparation and the filler (talc) is used in the amount of 99 parts by weight.

Deposition of the preparation on the adhesive tape, cutting thereof into strips and fixation of the latter to basal parts of tomato racemes are effected following the procedure described hereinabove. As a result, the number of fruits in bunches of tomatoes is increased by 5.4% and cropping power-by 4.8% as compared to corresponding characteristics of tomato plants non-treated with the preparation.

EXAMPLE 20

A powder-like preparation is produced on the basis of a phytohormone-auxin (heteroauxin) and a low-molecular carbohydrate (saccharose). To this end, 0.5 part by weight of heteroauxin is dissolved in 100 parts by weight of water. To the resulting solution is added, under thorough stirring, 99.5 parts by weight of saccharose. The thus-prepared slurry-like mass is dried and finely divided to a powder-like condition.

The resulting preparation is deposited by dusting onto an adhesive tape at the rate of 5 mg of the preparation per 1 cm$^2$ of the tape area, whereafter the tape is cut to strips of 2×3 mm size. Said strips are fixed in a ring-like manner to basal parts of grape cuttings prior to planting the cuttings into the soil.

As a result, the number of roots of the cuttings is increased by 19.6%, their length—by 26.7% as compared to cuttings of grapes non-treated with the preparation.

For the purpose of comparison, a powder-like preparation is produced on the basis of the same phytohormone, with the only difference that saccharose is not used in the composition of the preparation and a filler (china clay) is added in the amount of 99.5 parts by weight.

Deposition of the preparation on the adhesive tape, cutting thereof to strips and fixation of the latter to basal parts of grape cuttings are effected following the above-described procedure. As a result, the number of roots of cuttings is increased by 7.3% and their length—by 14.3% as compared to corresponding characteristics of grape cuttings non-treated with the preparation.

EXAMPLE 21

A preparation on the basis of a phytohormone-auxine (indolylbutyric acid) and a low-molecular carbohydrate (glucose) is produced. To this end, 0.005 part by weight of indolylbutyric acid and 10 parts by weight of glucose are dissolved in 89.995 parts by weight of water.

Green cuttings of roses are placed into the thus-prepared aqueous solution of the preparation for 15 hours prior to planting.

As a result, the number of rooted cuttings of roses is increased by 32.7%, the number of roots—by 36%, the root length—by 26.1% as compared to corresponding characteristics of rose cuttings non-treated with the preparation.

For the purpose of comparison, a preparation in the form of a solution is produced on the basis of the same phytohormone, with the only difference that glucose is not used in the composition of the preparation and water is taken in the amount of 99.995 parts by weight.

The thus-produced preparation is used to treat green cuttings of roses as described hereinabove. As a result, the number of roots rose cuttings is increased by 20.1% and the number of roots—by 20.1%, the root length—by 18% as compared to corresponding characteristics of rose cuttings non-treated with the preparation.

EXAMPLE 22

A preparation in the form of a solution is produced on the basis of a phytohormone-auxine (2,4,5-trichlorophenoxyacetic acid) and a low-molecular carbohydrate (saccharose). To this end, 0.005 parts by weight of 2,4,5-trichlorophenoxyacetic acid is dissolved in 89.995 parts by weight of water, whereafter 10 parts by weight of saccharose are added thereto under thorough stirring.

Into the thus-produced solution of the preparation immersed mersed for a short-time period (2-3 seconds) are inflorescences of tomatoes during the period of mass blossoming. As a result, the number of set fruits is increased by 36%, and cropping power—by 21.3% as compared to similar characteristics of tomato plants non-treated with the preparation.

For the purpose of comparison a solution of a preparation is made on the basis of the same phytohormone, with the only difference that saccharose is not used in the composition of the preparation and water is taken in the amount of 99.995 parts by weight.

This preparation is used to treat tomato inflorescences in a manner similar to that described hereinabove. As a result, the number of set fruits is increased by 16.1% and cropping power—by 12.3% as compared to corresponding characteristics of tomato plants non-treated with the preparation.

EXAMPLE 23

A preparation in the form of a solution is prepared on the basis of a phytohormone(cytoquinine), a plant growth inhibitor (chlorocholine chloride) and a low-molecular carbohydrate (glucose). To this end, 0.0001 part by weight of cytoquinine and 0.20 part by weight of chlorocholine chloride are dissolved in 91.7999 parts by weight of water, whereafter 8 parts by weight of glucose are added to the solution under thorough stirring.

The resulting solution of the preparation is used to spray grape bushes during the spring-summer period in the case of leaf chlorosis.

As a result, the amount of chlorophyll in leaves is increased by 24%, an intensive greening thereof is observed, growth of shoots is increased by 10.6% and cropping power—by 19.7% as compared to similar characteristics of grape bushes non-treated with the preparation.

For the purpose of comparison, a preparation in the form of a solution is prepared on the basis of the same phytohormone and the same plant growth inhibitor, with the only difference that glucose is not used in the composition of the preparation and water is taken in the amount of 99.7999 parts by weight.

The resulting preparation is used to treat grape bushes following the procedure described hereinabove.

As a result, the amount of chlorophyll in leaves is increased by 12.3%, a slightly pronounced greening thereof is observed; growth of shoots is increased by 4.11% and cropping power—by 11.2% as compared to corresponding characteristics of grape bushes non-treated with the preparation.

EXAMPLE 24

A preparation in the form of a solution is produced on the basis of a plant growth inhibitor, i.e. chlorocholine chloride, and a polyhydric alcohol, i.e. sorbitol. To this end, 0.25 parts by weight of chlorocholine chloride is dissolved in 93.75 parts by weight of water, whereafter 6 parts by weight of sorbitol are added to the solution under thorough stirring.

The thus-produced solution of the preparation is used to spray apple trees during the spring-summer period of an intensive growth of shoots. As a result, the growth of shoots is decreased by 25.6% and the number of fruit buds is increased thus contributing to an increased cropping power the next year after the treatment by 32.6% as compared to similar characteristics of apple trees non-treated with the preparation.

For the purpose of comparison, a preparation in the form of a solution is produced on the basis of the same plant growth inhibitor, with the only exception that sorbitol is not used in the composition of the preparation and water is taken in the amount of 99.75 parts by weight.

The thus-produced preparation is used to treat apple trees following the above-described procedure. As a result, growth of shoots is decreased by 14.6%, the number of fruit-buds is increased thus contributing to an increased cropping power the next year after the treatment by 21% as compared to corresponding characteristics of apple trees non-treated with the preparation.

EXAMPLE 25

A preparation in the form of a solution is prepared on the basis of a plant growth inhibitor, i.e. chlorocholine chloride and a polyhydric alcohol (mannitol). To this end, 0.20 part by weight of chlorocholine chloride is dissolved in 94.8 parts by weight of water, whereafter 5 parts by weight of mannitol are added to the solution under thorough stirring.

The thus-produced preparation in the form of a solution is used to spray lilac plants during the period of an intensive growth of shoots. As a result, the number of shoots with inflorescences is increased the next year after the treatment by 37.3% as compared to the corresponding characteristic of lilac plants non-treated with the preparation.

For the purpose of comparison, a preparation is produced in the form of a solution on the basis of the same plant growth inhibitor, with the only difference that mannitol is not used in the composition of the preparation and water is taken in the amount of 99.8 parts by weight.

The thus-produced preparation is used to treat lilac plants following the procedure described hereinabove. As a result, the number of shoots with inflorescences is increased the next year after the treatment by 18.9% as compared to the corresponding characteristic of lilac plants non-treated with the preparation.

EXAMPLE 26

A preparation in the form of a solution is prepared on the basis of a plant growth inhibitor (2,4-dichlorophenoxyacetic acid) and a low-molecular carbohydrate (saccharose). To do so, 0.2 part by weight of 2,4-dichlorophenoxyacetic acid is dissolved in 3 parts by weight of ethanol and then to the solution there are added 95.8 parts by weight of water and 4 parts by weight of saccharose.

The thus-produced solution of the preparation is used for spraying of weed plants in sowings of wheat during the spring-summer period. As a result, weeds of dicotyledonous plants are killed by 96%.

For the purpose of comparison a preparation is produced in the form of a solution on the basis of the same plant growth inhibitor, with the only exception that glucose is not used in the composition of the preparation and water is used in the amount of 99.8 parts by weight.

The thus-obtained solution of the preparation is used to treat weeds in seedlings of wheat following the procedure described hereinabove. As a result, weeds of dicotyledonous plants are killed by 67.9%.

EXAMPLE 27

A preparation in the form of a solution is prepared on the basis of a plant growth inhibitor (2-methyl-4-chlorophenoxyacetic acid) and a low-molecular carbohydrate (saccharose). To this end, 0.1 part by weight of 2-methyl-4-chlorophenoxyacetic acid is dissolved in 3 parts by weight of ethanol and then 94.9 parts by weight of water are added to the solution under thorough stirring along with 5 parts by weight of saccharose.

The thus produced solution of the preparation is used for spraying weeds in sowings of barley during the spring-summer period. As a result, weeds of dicotyledonous plants are killed by 98.3%.

For the purpose of comparison a preparation in the form of a solution is produced on the basis of the same plant growth inhibitor, except that saccharose is not included into the composition of the preparation, while water is taken in the amount of 99.9 parts by weight.

The thus-produced solution of the preparation is used to treat weeds of barley sowings following the procedure described hereinabove. As a result, weeds of dicotyledonous plants are killed by 64.2%.

EXAMPLE 28

A preparation in the form of a solution is prepared on the basis of an agent for treating plant diseases (copper sulphate) and a low-molecular carbohydrate (saccharose). To this end, 2 parts by weight of copper sulphate are dissolved in 93 parts by weight of water, whereafter 5 parts by weight of saccharose are added to the solution.

The resulting solution of the preparation is used for spraying peach plants "over the green cone", i.e. during the period of bud growing and emergence of first leaves for the purpose of treating curl disease of peach leaves.

As a result, the degree of injury of peach leaves by curl disease is reduced by 99.8%.

For the purpose of comparison, a preparation in the form of a solution is produced on the basis of the same agent for treating plant diseases, but saccharose is not used in the composition of the preparation and water is taken in the amount of 98 parts by weight. The thus-produced solution of the preparation is used to treat peach plants as described hereinabove. As a result, injury of peach leaves by curl disease is reduced by 78.6%.

EXAMPLE 29

A preparation in the form of a solution is produced on the basis of an agent for treating plan diseases (formaldehyde) and a low-molecular carbohydrate (saccharose). To this end, 0.3 part by weight of formaldehyde is dissolved in 94.7 parts by weight of water, whereafter 5 parts by weight of saccharose are added to the solution under vigorous stirring.

The thus-produced solution of the preparation is used for spraying of apricot plants during the spring period for the purpose of controlling the disease "bacterial blight". As a result, the degree of injury of shoots is reduced by 94.3%.

For the purpose of comparison, a preparation in the form of a solution is produced on the basis of the same agent for control of plant diseases, though saccharose is not included in the composition of the preparation, while water is taken in the amount of 99.7 parts by weight.

The thus-produced preparation solution is used for treating apricot plants following the procedure described hereinabove. As a result, the degree of injury of shoots is reduced by 26.8%.

EXAMPLE 30

A preparation in the form of a solution is produced on the basis of an agent for treating plant diseases (pararodaniline) and a low-molecular carbohydrate (fructose). To this end, 0.1 parts by weight of pararodaniline is dissolved in 94.90 parts by weight of water, whereafter 5 parts by weight of fructose are added thereto under stirring.

The thus-produced solution of the preparation is used for spraying rose plants during the summer period against mildew.

As a result, the degree of plant injury is reduced by 96.8%.

For the purpose of comparison, a preparation in the form of a solution is produced on the basis of the same agent for controlling plant diseases, but fructose is not used in the composition of the preparation and water is taken in the amount of 99.90 parts by weight.

The resulting solution of the preparation is used for spraying rose plants following the procedure described hereinabove. As a result, the degree of injury of rose plants is reduced by 65.3%.

EXAMPLE 31

A preparation in the form of a solution is produced on the basis of an agent for controlling plant diseases (ethylmercurophosphate) and a low-molecular carbohydrate (saccharose). To this end, 0.1 part by weight of ethylmercurophosphate is dissolved in 95.9 parts by weight of water, whereafter 4 parts by weight of saccharose are added to the solution under stirring.

The thus-produced solution of the preparation is used for spraying of apricot and peach plants in the summer period to control bacterial drying of shoots. As a result, the degree of injury of the plants with the disease is reduced by 98.3%.

For the purpose of comparison a preparation in the form of a solution is produced on the basis of the same agent for controlling plant diseases, though saccharose is not used in the composition of the preparation, while water is taken in the amount of 99.9 parts by weight. The resulting solution is used for spraying apricot and peach plants following the procedure described hereinabove. As a result, bacterial drying of shoots is reduced by 49.3%.

EXAMPLE 32

A preparation in the form of a solution is produced on the basis of agents for controlling plant diseases (streptomycin and penicillin) and a low-molecular carbohydrate (saccharose). To this end, 0.0001 part by weight of streptomycin and 0.0001 part by weight of penicillin are dissolved in 93.9998 parts by weight of water, whereafter 6 parts by weight of saccharose are added to the solution under stirring.

The thus-produced solution of the prepara .on is used for spraying sproutings of potato 10-20 days after emergence of sproutings in order to control phytophthora.

As a result, the degree of injury of potato with phytophthora is reduced to 12.3%.

For the purpose of comparison, a solution of the preparation is prepared on the basis of the same agents for controlling plant diseases, but saccharose is not used in the composition of the preparation and water is taken in the amount of 99.9998 parts by weight.

The resulting solution of the preparation is used for spraying potato sproutings following the above-described procedure. As a result, the degree of injury of potato with phytophthora is reduced to 47.2%.

EXAMPLE 33

A preparation in the form of a solution is produced on the basis of an agent for pest control (thiophos) and a low-molecular carbohydrate (saccharose). To this end, 0.05 part by weight of thiophos are dissolved in 94.95 parts by weight of water, whereafter 5 parts by weight of water are added to the solution under stirring.

The resulting solution of the preparation is used for spraying of cucumbers at the end of spring or in summer for controlling aphid.

As a result, a 100% aphid killing effect is observed. The period of action of the preparation, due to its increased penetration into plants, is prolonged to 25-30 days.

For the purpose of comparison, a preparation in the form of a solution is produced on the basis of the same agent for pest control, though saccharose is not used in the composition of the preparation and water is taken in the amount of 99.95 parts by weight.

Cucumbers are treated with the solution of the preparation following the procedure described hereinabove. As a result a 85% aphid killing effect is observed. The period of action of the preparation is up to 15 days.

EXAMPLE 34

A preparation in the form of a solution is produced on the basis of a plant pest control agent (methylmercaprophos) and a polyhydric alcohol (mannitol). To this end, 1 part by weight of methylmercaptophos is dissolved in 95 parts by weight of water, whereafter 4 parts by weight of mannitol are added thereto under stirring.

The thus-produced solution of the preparation is used for spraying apple trees in spring or summer for control of fruit mites.

As a result, fruit mites are killed by 98.6%. The period of action of the preparation, due to its increased penetration into plants, is prolonged up to 25-30 days.

For the purpose of comparison, a preparation in the form of a solution is produced on the basis of the same plant pest control agent, but mannitol is not incorporated in the composition of the preparation and water is employed in the amount of 99 parts by weight.

The thus-produced preparation is used for treating apple trees following the procedure described hereinabove. As a result, fruit mite killing of up to 78.3% is observed. The period of action of the preparation is up to 15 days.

EXAMPLE 35

A preparation in the form of a solution is produced on the basis of a plant pest control agent (octamethyl) and a low-molecular carbohydrate (saccharose). To this end, 0.1 part by weight of octamethyl is dissolved in 95.9 parts by weight of water, whereafter 4 parts by weight of saccharose are added to the solution under stirring.

The resulting solution of the preparation is used for spraying, during the entire vegetation period, wood plant varieties for the purpose of killing aphids and mites.

As a result, percentage of killed aphids and mites is within the range of from 85 to 97%. The period of action of the composition is 20 to 25 days.

For the purpose of comparison, a preparation in the form of a solution is produced on the basis of the same plant pest control agent, though saccharose is not used in the composition of the preparation.

The thus-produced preparation is used for spraying wood plant varieties (trees and bushes) following the above-described procedure. As a result, percentage of killed aphids and mites ranges from 60 to 80%. The period of action of the preparation is up to 15 days.

EXAMPLE 36

A preparation in the form of a solution is produced on the basis of a plant growth inhibitor (chlorocholine chloride) and a low-molecular carbohydrate (saccharose). To this end, 0.2 part by weight of chlorocholine chloride is dissolved in 95.8 parts by weight of water, whereafter 4 parts by weight of saccharose are added to the solution under stirring.

The thus-produced preparation is used for spraying, during the period of an intensive growth of shoots (May-June), of grapes for a better generative development of buds.

As a result, the number of inflorescences the second year after the treatment is increased by 27% and cropping power—by 24.5%.

For the purpose of comparison, a preparation in the form of a solution is produced on the basis of the same plant growth inhibitor, but saccharose is not incorporated into the composition of the preparation and water is taken in the amount of 99.8 parts by weight.

The thus-produced solution of the preparation is used for treating grapes following the procedure described hereinabove. As a result, the number of inflorescences the second year after the treatment is increased by 12.6%, and cropping power—by 13.6%.

EXAMPLE 37

A powder-like preparation is produced on the basis of a plant growth inhibitor (chlorocholine chloride), a low-molecular carbohydrate (saccharose) and a filler (grape vine ash). To this end, 2 parts by weight of chlorocholine chloride are dissolved in 100 parts by weight of water). Thereafter, 48 parts by weight of saccharose are added to the resulting solution under thorough stirring, followed by the addition of 50 parts by weight of grape vine ash. The thus-produced slurry-like mass is dried and finely divided to a powder-like condition.

The resulting preparation is deposited by dusting onto an adhesive tape at the rate of 5 mg of the preparation per 1 cm² of the tape surface area. Then the adhesive tape with the preparation deposited thereon is cut to strips with the size of 2×3 cm. Said strips are fixed in a ring-like manner onto basal parts of grape shoots 10 days before the beginning of blossoming.

Also produced is a powder-like preparation on the basis of a phytohormone (gibberellin) and a low-molecular carbohydrate (saccharose). To this end, 10 parts by weight of gibberellin are dissolved in 50 parts by weight of ethanol. To the resulting solution is added 100 parts by weight of water and then 90 parts by weight of saccharose. The resulting slurry-like mass is dried and finely divided to a powder-like condition.

The thus-produced preparation is deposited by dusting onto an adhesive tape at the rate of 5 mg of the preparation per 1 cm² of the tape area. Then the adhesive tape with the preparation deposited thereon is cut to strips with the size of 2×3 cm. Said strips are fixed in a ring-like manner on basal parts of inflorescences of the same grape bushes 10 days after the beginning of blossoming.

As a result, the growth of grape shoots is decreased by 24.7%, average weight of individual grapes is increased twice and total cropping power—by 1.9 times. The second year after the treatment with the two preparations the cropping power is increased by 35.8%.

As it is seen from the foregoing Examples 1 through 37, polyhydric alcohols and low-molecular carbohydrates readily penetrate into plants and are transported therein along with chemical agents thus contributing to a more rapid effect of physiological activity of the latter. This, in turn, makes it possible to control growth and generative development of plants, more effectively use preparations for controlling plant pests and diseases, as well as to increase cropping power of plants.

What is claimed is:

1. A method of introducing a biologically active chemical agent into plants whereby rapid penetration of said chemical agent into said plants occurs and the activity of said chemical agent is substantially enhanced comprising applying to a plant an effective amount of a composition in the form of a powder or an aqueous solution containing said chemical agent in admixture with a penetrating enhancing agent selected from the group consisting of water soluble low molecular weight polyhydric alcohols and water soluble low-molecular weight carbohydrates.

2. A method according to claim 1, wherein said penetrating enhancing agent is a polyhydric alcohol selected from the group consisting of dulcitol, arabitol, mannitol and sorbitol.

3. A method according to claim 1, wherein said penetration enhancing agent is a sugar selected from sucrose, glucose and fructose.

4. A method according to claim 1, wherein said composition is in the form of a powder which is applied to said plant by means of an adhesive tape on which said powdered composition has been deposited.

5. A method according to one of claims 1 or 4, wherein said composition is applied to the basal parts of plant organs.

6. A process according to one of claims 1 or 4, wherein said composition contains as said active chemical agent an active component, selected from the group consisting of macroelements, trace elements, vitamins, phytohormones, plant growth inhibitors, agents for plant disease control, agents for plant pest control and mixtures thereof.

7. A method according to claim 6, wherein said composition contains as said active chemical agent a macroelement selected from at least one member of the group consisting of nitrogen, phosphorus and potassium.

8. A method according to claim 1, wherein said composition contains as said active chemical agent a trace element selected from at least one member of the group consisting of boron, zinc and manganese.

9. A method according to claim 6, wherein said composition contains as said active chemical agent a vitamin selected from at least one member of the group consisting of thiamine and ascorbic acid.

10. A method according to claim 6, wherein said composition contains as said active chemical agent a phytohormone selected from at least one member of the group consisting of gibberellin, auxin and cytoquinine.

11. A method according to claim 6, wherein said composition contains as said active chemical agent a plant growth hormone selected from at least one member of the group consisting of chlorocholine chloride, 2,4-dichlorophenoxyacetic acid and 2-methyl-4-chlorophenoxyacetic acid.

12. A method according to claim 6, wherein said composition contains as said active chemical agent a plant disease control agent selected from at least one member of the group consisting of copper sulphate, formaldehyde, pararodaniline, ethylmercurophosphate, penicillin and streptomycin.

13. A method according to claim 6, wherein said composition contains as said active chemical agent an agent for plant pest control thiophos, methylmercaptophos and octamethyl.

14. A method according to one of claims 1 or 4, wherein said composition is in the form of a powder which further contains an inert solid filler.

15. A method according to claim 14, wherein said filler is selected from china clay, talc and plant ash.

16. A method of effecting the rapid penetration of a biologically active chemical agent into a plant and of enhancing the activity of said agent comprising applying said chemical agent to said plant in a composition containing said chemical agent in admixture with an penetration enhancing agent which is a water soluble, low molecular weight polyhydric alcohol or carbohydrate.

17. A method according to claim 16 in which said composition is in the form of a powder or an aqueous solution.

18. A method according to claim 16, wherein said composition is in the form of a powder which is applied to said plant by means of an adhesive tape on which said powdered composition has been deposited.

19. A method according to one of claims 1, 4, 16 or 18 in which said penetration enhancing agent is present in said composition in an amount of by weight of at least about 0.6 parts per part of said active chemical agent.

20. A method according to one of claims 1, 4, 16 or 18 in which said penetration enhancing agent is present in said composition in an amount of by weight of about 0.6 to about 33,000 parts per part of said active chemical agent.

21. A method according to one of claims 1, 16 or 18 in which said composition is in the form of an aqueous solution consisting essentially of said active chemical agent and said penetration enhancing agent.

22. A method according to one of claims 1, 4, 16 or 18 in which said composition is in the form of a powder and consists essentially of said active chemical agent and said penetration enhancing agent.

23. A method according to one of claims 1, 4, 16 or 18 in which said composition is in the form of a powder and consists essentially of said active chemical agent, said penetration enhancing agent and solid inert filler.

* * * * *